United States Patent [19]

Muller

[11] Patent Number: 5,019,074
[45] Date of Patent: *May 28, 1991

[54] LASER REPROFILING SYSTEM EMPLOYING AN ERODABLE MASK

[75] Inventor: David F. Muller, Boston, Mass.

[73] Assignee: Summit Technology, Inc., Waltham, Mass.

[*] Notice: The portion of the term of this patent subsequent to Aug. 15, 2006 has been disclaimed.

[21] Appl. No.: 392,782

[22] Filed: Aug. 11, 1989

Related U.S. Application Data

[63] Continuation-in-part of Ser. No. 19,200, Mar. 9, 1987, Pat. No. 4,856,513, which is a continuation-in-part of Ser. No. 124,101, Jan. 15, 1988.

[51] Int. Cl.$^5$ ............................................. A61N 5/06
[52] U.S. Cl. ........................................ 606/5; 606/13; 128/395; 128/898; 350/363; 219/121.6; 219/121.67; 219/121.69; 219/121.73; 219/121.85
[58] Field of Search ............... 128/345, 348, 397, 898; 606/3-5, 13; 219/121.6, 121.67, 121.68, 121.69, 121.7, 121.71, 121.72, 121.73, 121.74, 121.75, 121.85; 350/363

[56] References Cited

U.S. PATENT DOCUMENTS

| | | | |
|---|---|---|---|
| 3,558,208 | 1/1971 | Hudson | 350/314 |
| 3,703,176 | 11/1972 | Vassilliadis et al. | 128/394 |
| 3,769,963 | 11/1973 | Goldman et al. | 128/2 R |
| 3,941,973 | 3/1976 | Luck, Jr. et al. | 219/121 |
| 3,982,541 | 9/1976 | L'Esperance, Jr. | 128/303.1 |
| 4,173,980 | 11/1979 | Curtin | 128/303 R |
| 4,266,549 | 5/1981 | Kimura | 128/303.1 |
| 4,309,998 | 1/1982 | Aaron nee Rosa et al. | 128/303.1 |
| 4,326,529 | 4/1982 | Doss et al. | 128/303.1 |
| 4,381,007 | 4/1983 | Doss | 128/303.1 |
| 4,461,294 | 7/1984 | Baron | 128/303.1 |
| 4,527,043 | 7/1985 | Hashiura et al. | 219/121 |
| 4,538,608 | 9/1985 | L'Esperance, Jr. | 128/303.1 |
| 4,648,400 | 3/1987 | Schneider et al. | 128/303.1 |
| 4,665,913 | 5/1987 | L'Esperance, Jr. | 128/303.1 |
| 4,669,466 | 6/1987 | L'Esperance | 128/303.1 |
| 4,686,979 | 8/1987 | Gruen et al. | 128/303.1 |
| 4,718,418 | 3/1988 | L'Esperance, Jr. | 128/303.1 |
| 4,721,379 | 1/1988 | L'Esperance | 351/212 |
| 4,729,372 | 3/1988 | L'Esperance, Jr. | 128/303.1 |
| 4,732,148 | 3/1988 | L'Esperance, Jr. | 128/303.1 |
| 4,770,172 | 9/1988 | L'Esperance, Jr. | 128/303.1 |
| 4,773,414 | 9/1988 | L'Esperance, Jr. | 128/303.1 |
| 4,798,204 | 1/1989 | L'Esperance, Jr. | 128/303.1 |
| 4,838,266 | 6/1989 | Koziol et al. | 606/5 |
| 4,856,513 | 8/1989 | Muller | 128/303.1 |

FOREIGN PATENT DOCUMENTS

| | | |
|---|---|---|
| 111060 | 6/1984 | European Pat. Off. . |
| 224322 | 6/1984 | European Pat. Off. . |
| 152686 | 8/1985 | European Pat. Off. . |
| 3148748 | 7/1983 | Fed. Rep. of Germany . |
| 353073 | 4/1987 | Fed. Rep. of Germany . |
| 3535072 | 4/1987 | Fed. Rep. of Germany . |
| WO86/04500 | 8/1986 | PCT Int'l Appl. . |

OTHER PUBLICATIONS

Fine et al., "Preliminary Osberations on Ocular Effects ...", vol. 64, No. 2, *American Journal of Ophthalmology* pp. 209–222 (Aug. 1967).

(List continued on next page.)

Primary Examiner—Stephen C. Pellegrino
Assistant Examiner—David Shay
Attorney, Agent, or Firm—Thomas J. Engellenner

[57] ABSTRACT

A laser system for reprofiling a surface comprising a laser and an erodable mask disposed between the laser means and the surface for providing a predefined profile of resistance to erosion by laser radiation, and control for controlling the laser such that upon irradiation of the mask, a portion of the laser radiation is selectively absorbed and another portion is transmitted to the surface in accordance with the mask profile to selectively erode the surface. The mask can be connected to the support structure and disposed in optical alignment with the laser means and the cornea. The mask can be directed integrated with the support structure or, preferably, a transparent stage can be formed as part of the support structure to support and position the masking lens. In one preferred embodiment, the mask is spatially separated from the surface and imaged onto the surface, thereby permitting the use of an oversized mask, which is easier to form.

19 Claims, 2 Drawing Sheets

OTHER PUBLICATIONS

Beckman, et al., "Limbectomies, Keratectomies, and Keratostomies Performed . . . " vol. 71, *American Journal of Opthalmology*, pp. 1277-1283 (Jun. 1971).

Mainster, "Opthlamic applications of infrared lasers--thermal considerations" vol. 18, No. 4, *Invst. Opthal. and Vis. Sci.*, pp. 414-420 (1979).

Peyman, et al, "Modification of Rabbit Corneal Curvature with use of Carbon Dioxide Laser Burns", vol. No. 11, No. 5, *Opthalmic Surgery*, pp. 325-329 (May 1980).

Keates et al., "Carbon Dioxide Laser Beam Control for Corneal Surgery", vol. 12, No. 2, *Opthalmic Surgery*, pp. 117-122, (Feb. 1981).

Girard, "Refractive Keratoplasty", vol. 2, *Corneal Surgery*, pp. 142-171 (1981).

Taboada et al., "Response of the Corneal Epithelium to KrF Excimer Laser Pulses", vol. 40, *Health Physics*, pp. 677-683 (May 1981).

Chetverukhin et al., "Refraction Thermokeratoplasty and Laser Keratoplasty", *Vestn. Oftal.*, pp. 67-69 (USSR 1982).

Srinivasan et al., "Far-UV Photoetching of Organic Material", *Laser Focus*, (May 1983).

Srinivasan, "Kinetics of the Ablative Photodecomposition of Organic Polymers . . ", vol. B1, *J. of Vac. Sci. Technol.*, pp. 923-926 (1983).

Srinivasan, "Action of Far-Ultraviolet Light on Organic Polymer Films . . .", pp. 12-14 (Oct. 1983).

Trokel, et al., "Excimer Laser Surgery of the Cornea", vol. 96, *American Journal of Opthalmology*, pp. 710-715 (1983).

Galbavy, "Use of Diamond Knives in Ocular Surgery", vol. 15, No. 3, *Opthalmic Surgery*, pp. 203-205 (Mar. 1984).

Puliafito et al., "Excimer Laser Ablation of the Cornea and Lens", vol. 92, No. 6, *Opthalmology*, pp. 741-748 (Jun. 1985).

L'Esperance, Jr., "New Laser Systems and Their Potential Clinical Usefulness", *Trans. New Orleans Acad. of Opthalmol.*, pp. 182-209 (1985).

L'Esperance, Jr., "Current Status of Opthalmic Photovaporization Therapy", *Trans. New Orleans Acad. of Opthalmol,* pp. 231-255 (1985).

O'Hara et al., vol. 11 *IBM Technical Disclosure Bulletin* pp. 1168-1169 (1969).

Binder et al., "Refractive Keratoplasty" vol. 100 *Arch. Opthalmol.* pp. 802-806 (1982).

LASER REPROFILING SYSTEM EMPLOYING AN ERODABLE MASK

REFERENCE TO RELATED APPLICATIONS

This application is a continuation-in-part of U.S. Ser. No. 019,200, filed on Mar. 9, 1987 now U.S. Pat. No. 4,856,513, and U.S. Ser. No. 124,101, filed on Jan. 15, 1988.

BACKGROUND OF THE INVENTION

The technical field of this invention is laser ablation of surfaces, especially surfaces of biological materials. In particular, the invention relates to systems and methods for reprofiling the cornea of the eye.

It is known to employ laser sources to erode surfaces of workpieces and the like. Such apparatus is in general relatively complex and demands highly skilled use. It is an object of the present invention to provide improved and simplified apparatus and method for eroding surfaces.

It is also an object of the present invention to provide an improvement whereby laser techniques can be applied to sensitive surfaces and, in particular, to objects in which it would be undesirable to affect underlying layers.

In the field of medicine, a known technique for the treatment of certain forms of myopia is surgically to remove a segment of the collagen sub-surface layer of the eye, to reshape the removed segment as by surgical grinding, and to restore the reshaped segment in the eye. The eye heals by reformation of the outer cellular layer over the reshaped collagen layer. Alternatively, a layer of the cornea is opened up as a flap, an artificial or donor lenticular implant is inserted under the flap, and the flap is sutured up again.

It is a further object of this invention to provide an improved and less traumatic method and apparatus for reshaping the cornea of the eye.

Various other surgical techniques for reprofiling of the corneal surface have also been proposed. One increasingly common technique is radial keratotomy, in which a set of radial incisions, i.e., resembling the spokes of a wheel, are made in the eye to remedy refractive errors such as myopia (nearsightedness). As the incisions heal, the curvature of the eye is flattened, thereby increasing the ocular focal distance. The operation is not particularly suitable for correction of hyperopia (farsightedness) and can pose problems if the surgical incisions are uneven or too deep.

The use of a laser beam as a surgical tool for cutting incisions, a so-called laser scalpel, has been known for some time (see, for example, Goldman et al. U.S. Pat. No. 3,769,963). In 1980, a study was made of the damage which might be inflicted on the corneal epithelium by exposure to the recently developed excimer laser (see Taboada et al., "Response of the Corneal Epithelium to ArF excimer laser pulses" *Health Physics* 1981, Volume 40, pp. 677-683). At that period, surgical operations on the cornea were commonly carried out using diamond or steel knives or razor, and further, such techniques were still being studied (see, for example, Binder et al., "Refractive Keratoplasty" *Arch. Ophthalmol.* May 1982, Vol. 100, p. 802). The use of a physical cutting tool in corneal operations, and the insertion of an implant under a flap, continue to be widely practiced up to the present day (see for example "Refractive Keratoplasty improves with Polysulfone, Pocket Incision" *Ophthalmology Times.* July 1, 1986).

It has been suggested in U.S. Pat. No. 4,665,913 issued to L'Esperance that controlled ablative photodecomposition of one or more selected regions of a cornea can be performed using a scanning action on the cornea with a beam from an excimer laser. Because of the scanning action, it is necessary for L'Esperance to bring his laser beam to a small spot, typically a rounded-square dot of size 0.5 mm by 0.5 mm.

L'Esperance suggests that myopic and hyperopic conditions can be reduced by altering the curvature of the outer surface of the cornea by repeatedly scanning the cornea with an excimer laser beam having this standard, small spot size but varying the field which is scanned during successive scans, so that some areas of the cornea are scanned more often than others. In this way, it is claimed, the surface can be eroded by different amounts depending on the number of times the spot scans the surface. Additionally, he suggests that certain severe myopic and hyperopic conditions may be treated with a reduced removal of tissue by providing the outer surface of the cornea with a new shape having Fresnel-type steps between areas of the desired curvature.

In practice, complex apparatus is required to cause a pulsed laser beam to scan with the precision required if the eroded surface is to be smooth. Thus, if successive sweeps of a scan overlap, there will be excessive erosion in the overlap area, whereas if they fail to meet, a ridge will be left between the sweeps. The pulsed nature of excimer laser radiation also tends to exacerbate this problem. Additionally, the scanning method is inherently time-consuming even with highly refined techniques and apparatus, since the laser beam is only eroding a very small part of the total area to be treated at any given moment. Furthermore, such a scanning system can cause rippling effects on relatively soft materials such as corneal tissue.

It is therefore a further object of the present invention to provide a method and apparatus for eroding a surface using a laser which does not require scanning of the area of the surface to be eroded.

Another technique for corneal reshaping involves the use of a laser photoablation apparatus in which the size of the area on the surface, to which the pulses of laser energy are applied, is varied to control the reprofiling operation. In one preferred embodiment, a beam-shaping stop or window is moved axially along the beam to increase or decrease the region of cornea on which the laser radiation is incident. By progressively varying the size of the exposed region, a desired photoablation profile is established in the surface. For further details on this technique see also, Marshall et al., "Photo-ablative Reprofiling of the Cornea Using an Excimer Laser: Photorefractive Keratoctomy", Vol. 1, *Lasers in Ophthalmology*, pp. 21-48 (1986) herein incorporated by reference.

Although this technique for varying the size of the exposed region is a substantial improvement over physical shaping (i.e., scalpel) techniques and laser spot scanning protocols, a considerable number of optical elements and control systems still are required for precise operation, particularly on human corneal tissue. There exists a need for better and simpler procedures for shaping surfaces, particularly the surfaces of biological tissues, such as corneal tissue.

SUMMARY OF THE INVENTION

A laser system and masking apparatus are disclosed for reprofiling material surfaces. The system comprises a laser means and a masking means disposed between the laser means and the target surface. The laser means is collimated to provide a uniform beam of radiation to the masking means. The masking means provides a predefined profile of resistance to erosion by laser radiation, and includes a control means for controlling the laser such that upon irradiation of the masking means, a portion of the laser radiation is selectively absorbed and another portion is transmitted to the surface in accordance with the mask profile to selectively erode the surface.

The masking means can comprise a mask and a support structure, preferably affixed to the laser or otherwise optically aligned therewith, such that the laser beam selectively passes through the masking means and onto the target surface. The masking means can further comprise a transparent stage, which is attached to the support structure. The masking means may be independently fixed between the laser and surface, or it may be directly attached to the surface.

The masks of the present invention provide a predefined profile of resistance to erosion by laser radiation. Such profiles can be provided by varying the thickness or composition of the mask material. When the thickness of the mask is varied, the mask may be convex-concave, plano-convex, plano-concave, convex-convex or concave-concave, depending upon the nature of the desired erosion of the target surface. In addition, the masking lens may be aspheric or torroidal at least on one surface, or for special cases, such as the removal of ulcers, the surface shape may be irregular.

Conveniently, the mask material has similar ablation characteristics to the target surface. Various polymeric materials can be employed including, for example, poly(methyl methacrylate), poly(methyl styrene) and mixtures thereof. For corneal reprofiling, the ablation characteristics of the masking material can range from about $10^3$ to about $10^6$ cm$^{-1}$. Preferably, the masking material has an absorption characteristic of micron or submicron etch depths per pulse similar to those of the cornea when it is exposed to pulsed UV excimer laser radiation.

Alternately, the mask may be of uniform thickness but vary in composition to provide the desired profile of resistance to radiation.

The invention may further comprise any combination of mirrors, lenses and prisms, located either upstream or downstream of the masking means, or both, for imaging, focusing and redirecting the laser beam. Such configurations allow for the use of an oversized or undersized mask for greater convenience. Depending upon the application, the configuration of the optical elements may include focusing lenses, divergent lenses, and collimating lenses, in various combinations and in a variety of shapes well known to those skilled in the art.

According to another aspect of the invention, there is provided a method of reprofiling a surface comprising (a) optically aligning a laser means with a target surface, the laser means being operable to deliver laser radiation to the surface; and (b) disposing a masking means between the laser means and the target surface, the masking means having a predefined profile of resistance to erosion by laser radiation such that upon irradiation a portion of the radiation is selectively absorbed and another portion is transmitted to the target surface in accordance with the mask profile to selectively erode the target surface.

The methods of the present invention are particularly well suited for controlled reprofiling of the cornea, particularly a region known as Bowman's membrane, which lies immediately below the uniform, extremely thin, epithelial layer of the cornea. The epithelial layer is very rapidly ablated on exposure to the laser light, and heals and eventually reforms following the reshaping operation. In surgical applications, the laser source is preferably an excimer laser, such as a UV Argon Fluoride laser operating at about 193 manometers, which does not penetrate through the cornea. A minimum laser irradiance level is essential for ablation, but it is preferred not greatly to exceed this minimum threshold.

The pulse repetition rate for the laser may be chosen to meet the needs of each particular application. Normally, the rate will be between 1 and 500 pulses/sec., preferably between 1 and 100 pulses/sec.

Suitable irradiation intensities vary depending on the wavelength of the laser and the nature of the irradiated object. For a given wavelength of laser energy applied to any given material, there will typically be a threshold value of the energy density below which significant erosion does not occur. Above the threshold density, there will be a range of energy density above which increasing energy densities give increasing depths of erosion, until a saturation level is reached. For increases in energy density above the saturation value, no significant increase in erosion occurs.

The threshold value and the saturation value will vary between wavelengths of laser energy and between target surface materials. However, for any particular laser wavelength and any particular material, the values can be found readily by experiment. For example, in ablation of the Bowman's membrane of the cornea alone or the membrane and the underlying corneal stroma by energy of wavelength 193 nm (the wavelength obtained from an ArF excimer laser), the threshold value is about 50 mJ per cm$^2$ per pulse, and the saturation value is about 250 mJ per cm$^2$ per pulse. There appears to be little benefit in exceeding the saturation value by more than a small factor, and suitable energy densities at the corneal surface are 50 mJ per cm$^2$ to one J per cm$^2$ per pulse for a wavelength of 193 nm.

The threshold value can vary very rapidly with wavelength. At 157 nm, which is the wavelength obtained from a F$_2$ laser, the threshold is about 5 mJ per cm$^2$ per pulse. At this wavelength, suitable energy densities at the corneal surface are 5 mJ per cm$^2$ to one J per cm$^2$ per pulse.

Most preferably, the laser system is used to provide an energy density at the surface to be eroded of slightly less than the saturation value. Thus, when eroding the cornea with a wavelength of 193 nm (under which conditions the saturation value is 250 mJ per cm$^2$ per pulse), it is preferable to provide to the erodable mask and cornea pulses of an energy density of 100 to 200 mJ per cm$^2$ per pulse. Typically, a single pulse will erode a depth in the range 0.1 to 1 micrometer of collagen from the cornea.

The invention will next be described in connection with certain illustrated embodiments; however, it should be clear that those skilled in the art can make various modifications, additions and subtractions without departing from the spirit or scope of the invention.

For example, the invention can be used in connection with corneal transplants or synthetic inlays where a donor insert is stitched into the patient's eye. Quite often, accidental over-tightening of the stitches introduces refractive errors in the cornea following the operation. At present, the transplant operation must be repeated or relaxing incisions must be made in the cornea. The present invention can provide an improved and less traumatic method for remedying such refractive errors.

Additionally, the present invention can be used to treat astigmatisms, corneal ulcers and keratomic growths which affect vision. In such instance, specific masks can be designed and constructed to selectively remove the corneal tissue which interfere with normal refraction.

Moreover, the teaching of the present invention can be applied to other biological tissues requiring reprofiling, including lenticular implants, ligaments, cartilage, and bone.

BRIEF DESCRIPTION OF THE DRAWINGS

The invention will now be described by way of example with reference to the accompanying drawings, in which.

DETAILED DESCRIPTION

Figure 1:
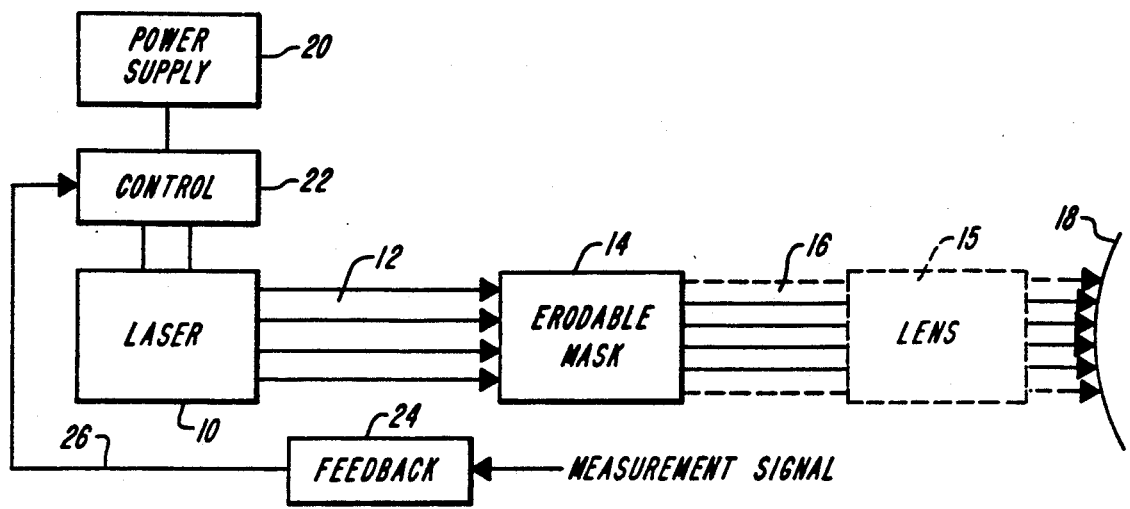
FIG. 1 is a schematic illustration of an apparatus for practicing a method of reprofiling the surface of an object, in accordance with the invention.

In FIG. 1, a laser 10 provides a radiation output 12 to an erodable mask 14 which provides a predefined profile of resistance to the radiation. A portion of the laser radiation 16 is selectively transmitted in accordance with the profile of mask 14 and irradiates the surface 18 of the object which is to be reprofiled and which as shown may comprise the cornea of an eye. The system can further include one or more imaging lens elements 15 to image the mask 14 onto the surface 18.

The laser is powered by a power supply unit 20 and control circuit 22 which can be adjustable to cause the laser to produce pulses of light at a specific frequency and intensity. To further control the laser, a feedback device 24 can be provided which receives information from optical or other inspection of the mask 14 and/or surface 18 while it is exposed to irradiation by the laser 10. A feedback path 26 communicates with the control circuit 22 for controlling the laser 10.

Figure 2:
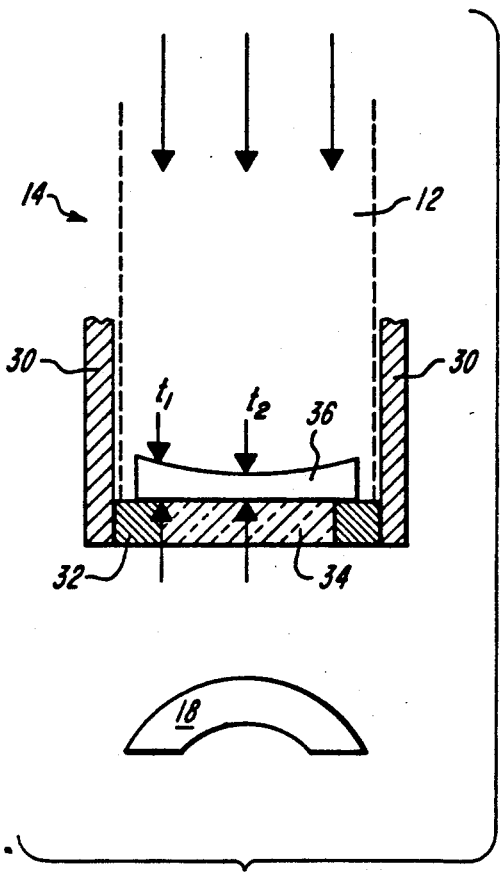
FIG. 2 is a more detailed illustration of an erodable mask suitable for use in the apparatus of FIG. 1.

In FIG. 2, one embodiment of the erodable mask 14 of FIG. 1 is shown in more detail. As illustrated, the erodable mask 14 includes a support structure 30, which may be rigidly connected to the laser device or otherwise optically aligned such that radiation 12 from the laser (through collimating means not shown) can be selectively transmitted through the mask to produce the desired erosion of the surface by pulses of laser energy.

At least a portion of the horizontal surface 32 is formed by a transparent stage 34, which allows laser radiation to pass through to the target surface. Preferably, the remainder of surface 32 is opaque to laser radiation. Disposed upon the horizontal surface 32 and the transparent stage 34 is masking lens 36.

In another embodiment, the transparent stage may include a lens system for focusing the profile of radiation that passes through the masking lens. This would enable the use of an oversized masking lens relative to the desired erosion of the target surface. Alternately, the transparent stage may include a lens system to spread out the profile of radiation that passes through the masking lens. This would enable the use of an undersized masking lens relative to the desired erosion of the target surface.

The selected mask material is erodable by laser radiation and preferably has ablation characteristics substantially identical to the object material. For example, the erodable masks of the present invention can be formed from plastic material such as poly(methyl methacrylate) (PMMA) or poly(methyl styrene) (PS). These polymers are both bio-compatible and can be efficiently eroded by laser radiation, i.e., by a pulsed ArF excimer laser (193 nm). These polymers are mutually soluble in each other, and by changing the concentration of PS in PMMA, absorption coefficients can be varied from about $10^3$ to about $10^6$ cm$^{-1}$. Other organic polymers exhibiting suitable ablation characteristics can also be employed in the manufacture of erodable masks. Preferably, the polymeric material has an absorption characteristic of micron or submicron etch depths per pulse similar to those of the cornea. For further details on organic polymers suitable for construction of masks, see Cole et al., "Dependence of Photo-etching Rates of Polymers at 193 nm on Optical Absorption Coefficients", Vol. 48 *Applied Physics letters*, pp. 76–77 (1986), herein incorporated by reference Various techniques can be employed to manufacture the lenses used in the present invention from PMMA or PS. These techniques included injection molding, casting, machining and spin casting. Manufacture by laser machining can also be employed. In one typical technique, a solution of PMMA or PS is prepared in toluene and spin cast in a suitably-shaped cup to obtain a smooth, uniform lens having a pre-defined profile thickness. Depending upon the concentration of PS in PMMA, a suitable absorption coefficient is obtained. The films can then be removed from the spin cup and vacuum baked to remove residual solvent.

Alternatively, the erodable mask can be made of a material having a variable composition such that predefined regions of the mask selectively absorb greater amounts of laser radiation even though the entire mask has a uniform thickness. Again, materials such as PMMA and PS can be employed in varying concentrations in the erodable mask to achieve the variable composition of the mask.

Figure 3:
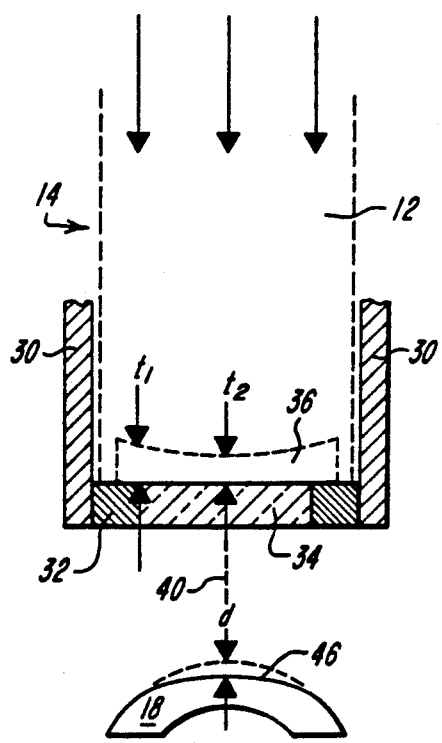
FIG. 3 illustrates diagrammatically the method of the present invention in reducing the curvature of an object.

FIG. 3 illustrates the principle involved in eroding a surface to effect reprofiling thereof in accordance with the present invention. Although the transparent stage shown in the figures is substantially horizontal, it should be clear that it can also take other shapes (e.g., concave or convex spherical forms) and can further include a cup-shaped rim to support a liquid, semi-liquid, or cured polymer masking lens.

In FIG. 3, the reference 18 denotes the object, such as the cornea of an eye, to be reprofiled. A uniform beam of radiation 12, obtained preferably from a pulsed UV laser source, irradiates mask 36. (A configuration of collimating lenses, well known to those in the art, may be used upstream of the mask 36 to provide a uniform, plane wave of radiation 12). The mask 36 is gradually and uniformly ablated, and an increasing area of radiation passes through transparent stage 34 and irradiates and erodes object 18.

According to the embodiment of mask 36 in FIG. 3, radiation 12 first wholly erodes location $t_2$, the thinnest part of the mask, and irradiates location d of object 18. Radiation 12 continues to ablate mask 36, and wholly erodes an area centered at location $t_2$ such that a column of radiation, increasing in diameter over time and centered along line 40, irradiates and erodes object 18 at region 46. The radiation source 12 stops irradiating mask 36 when the radius of the hole in the lens increases in size to radius $t_1$. At that moment in time, the resultant erosion 46 of object 18 corresponds to the size and shape of mask 36 prior to irradiation.

If the resistance to erosion of mask 36 is the same as the resistance to erosion of object 18, then the maximum depth of erosion d of object 18 is equal to the difference between the thicknesses of $t_1$ and $t_2$ of mask 36. The thickness of the profile of erosion decreases from a maximum depth d at location d in accordance with the thickness profile of masking lens 36. The erosion depth reaches zero thickness at a radius from location d corresponding to radius $t_1$ of mask 36. Alternately, the laser source may continue to irradiate object 18 after the active portion of the masking lens is wholly eroded, which would uniformly ablate the profiled portion of object 18 to a desired depth, leaving a ridge or crater effect at the perimeter.

The present invention is especially suited to the treatment of the cornea of an eye and provides a less dramatic means of effecting reprofiling of the cornea, for example, as a remedy for certain forms of refractive errors. FIGS. 2 and 3 illustrate the methods of the present invention in connection with the treatment of myopia (nearsightedness). Similar lenses of appropriate shape can, of course, be employed to remedy other forms of reflective errors, such as hyperopia and astigmatism.

For example, for the correction of astigmatism, the column of irradiation between mask 36 and object 18 in FIG. 3 will comprise an elliptical cross-sectional area, and radius location $t_1$ will be of varying distance from mask center $t_2$. Various other mask shapes may be used such that maximum thickness $t_2$ of mask 36 need not be at the center of the lens, nor need be limited to one location.

Alternately, if the mask has a uniform thickness but varying resistance to erosion, the depth of erosion of the target object will correspond to changes in the resistance to erosion instead of changes in lens thickness. In addition, the maximum thickness of erosion d of object 18 need not equal the difference in thickness between $t_1$ and $t_2$, such as if the resistance to erosion of the mask differs from that of the target object.

Figure 4:
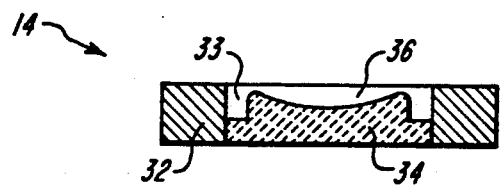
FIG. 4 illustrates another embodiment of an erodable mask suitable for use in the apparatus of FIG. 1.

FIG. 4 illustrates an alternative embodiment of the erodable mask 14 having a surface 32 formed in part by a cup-shaped, transparent stage 34. Disposed within the stage 34 is an erodable masking lens 36, which can be formed by deposition of a liquid polymer followed by in-situ curing of the polymer. The stage 34 can further include a rim cavity 33 which is likewise filled with a liquid polymer to serve as a reservoir of polymer during curing and thereby prevented shrinkage of the mask 36 as it solidifies.

Figure 5:
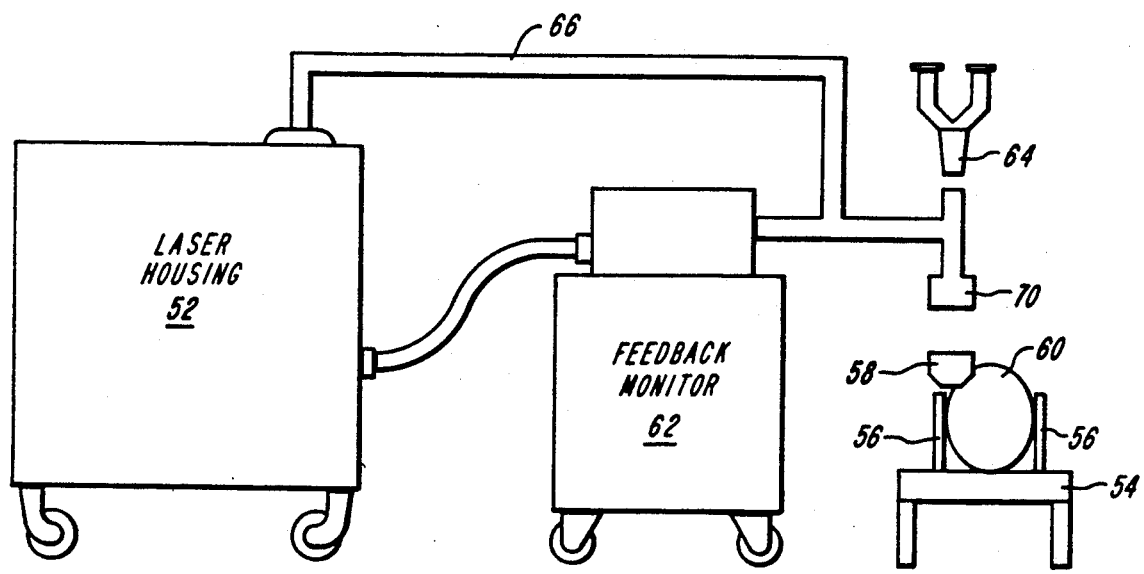
FIG. 5 shows a laser apparatus for measurement and reprofiling.

FIG. 5 illustrates an apparatus for performing a method of the present invention for reprofiling the cornea of a human eye. A laser and associated control circuitry is contained in a housing 52. The beam-forming optics, for providing a beam of desired shape and size, can also be contained within the housing 52 together with the laser power supply control circuits. An optical wave guide 66, which can be flexible or rigid and includes suitable mirrors, prisms and lenses, is provided to transmit the laser beam output from the housing 52 to the patient's head 60. The patient is lying face-upwards on an operating table 54. The operating table 54 will support the patient's head against vertical movement. If desired, side supports 56 may also be provided to restrain sideways movement of the patient's head 60.

An erodable mask, such as that shown in FIGS. 2 and 3, or FIG. 4 is disposed within masking apparatus 70 and is optically aligned with the patient's eye by markers disposed on immobilizing eyepiece 58, or by other techniques known in the art. The erodable mask is manufactured as described above based on measurements of the patient's eye and has an profile which will impart the desired refraction correction upon erosion.

During the operation, the eye can be observed using a surgical microscope 64 which is supported above the patient by any convenient means. The surgical microscope 64 may be connected to the erodable apparatus 70, but will more normally be separated therefrom and supported by an arm (not shown) from the ceiling or by a cantilever (not shown).

A measuring device 62 can also be employed in conjunction with the present apparatus to measure the changes in the curvature of the cornea following operation. Such a measuring device 62 can also be employed to monitor the degree of erosion of the mask during treatment. The measuring device can take the form of a commercially-available keratometer or other suitable device and can be connected, as shown in FIG. 5, directly to the laser optical path.

The measuring device 62 can further provide the feedback control, as shown in FIG. 11, whereby information from optical or other inspection of the surface which is being exposed to laser erosion is used to control the actual duration and amplitude of the pulses supplied by the laser and may be tuned so as to produce the desired degree of erosion of the surface by each pulse.

I claim:

1. A masking apparatus for use in laser reprofiling of a target surface, the apparatus comprising a support structure and an erodable mask connected to the support structure, the mask being erodable by radiation from a reprofiling laser and having a predefined profile of resistance to erosion by laser radiation, whereby upon irradiation of the mask, a portion of the laser radiation is selectively absorbed by the mask and another portion is transmitted to the target surface in accordance with the mask profile to selectively erode the target surface.

2. The apparatus of claim 1 wherein the mask which varies in thickness to provide the profile of resistance.

3. The apparatus of claim 1 wherein the mask varies in composition to provide the profile of resistance.

4. The apparatus of claim 1 wherein the mask is formed from poly(methyl methacrylate), poly(methyl styrene), or mixtures thereof.

5. The apparatus of claim 1 wherein the support structure further includes a transparent stage to which the mask is affixed.

6. The apparatus of claim 1 wherein the apparatus further includes at least one imaging lens for projecting radiation transmitted through the mask to the target surface.

7. A method of reprofiling a surface comprising:
  locating a laser means for generating a laser beam in optical alignment with a target surface, the laser means being operable to deliver laser radiation to the target surface; and
  disposing an erodable masking means between the laser means and the target surface, the masking means being erodable by radiation from the laser means and having a predefined profile of resistance to erosion by laser radiation such that upon irradiation a portion of the radiation is selectively absorbed by the masking means and another portion is transmitted to the target surface in accordance with the mask profile to selectively erode the target surface.

8. The method of claim 7 wherein the method further includes varying the thickness of the masking means to provide the profile of resistance.

9. The method of claim 7 wherein the method further includes varying the composition of the masking means to provide the profile of resistance.

10. The method of claim 7 wherein the masking means is formed from poly(methyl methacrylate), poly(methyl styrene), or mixtures thereof.

11. The method of claim 7 wherein the method further includes a transparent stage means to which the masking means is affixed and in which radiation passes through a selected region and is absorbed in another selected region.

12. The method of claim 7 wherein the method further includes at least one imaging lens means for projecting radiation transmitted through the masking means to the target surface.

13. The method of claim 7 wherein the target surface is biological tissue.

14. The method of claim 7 wherein the target surface is corneal tissue.

15. A masking apparatus for use in laser reprofiling of corneal tissue comprising a support structure and an erodable mask connected to the support structure and positionable above the cornea, the mask being erodable by radiation from a reprofiling laser and having a predefined profile of resistance to radiation from the laser whereby, upon irradiation of the mask, a portion of the laser radiation is selectively absorbed by the mask and another portion is transmitted to the cornea in accordance with the mask profile to selectively erode the tissue.

16. The apparatus of claim 15 wherein the support further includes a transparent stage for receiving the mask.

17. The apparatus of claim 15 wherein the mask varies in thickness to provide the profile.

18. The apparatus of claim 15 wherein the mask varies in composition to provide the profile.

19. The apparatus of claim 15 wherein the mask is formed from poly(methyl methacrylate), polymethylstyrene or mixtures thereof.

* * * * *